US006649339B1

(12) United States Patent
Zerlauth et al.

(10) Patent No.: US 6,649,339 B1
(45) Date of Patent: Nov. 18, 2003

(54) METHOD FOR PRODUCING A QUALITY ASSURED BIOLOGICAL SAMPLE AND COMPOSITION CONTAINING THE SAME

(75) Inventors: Gerold Zerlauth, Vienna (AT); Matthias Gessner, Gross Enzersdorf (AT); Karl Koettnitz, Deutsch Wagram (AT); Patricia Gross, Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/642,633

(22) Filed: Aug. 18, 2000

(51) Int. Cl.$^7$ .............................. C12Q 1/70; C12Q 1/68; C12Q 1/04; C12P 1/34
(52) U.S. Cl. ................................ 435/5; 435/6; 435/34; 435/91.2; 536/25.3
(58) Field of Search ........................ 435/5, 6, 34, 91.2; 536/25.9, 25.3

(56) References Cited

U.S. PATENT DOCUMENTS

| | | | |
|---|---|---|---|
| 4,613,501 A | 9/1986 | Horowitz | 424/89 |
| 4,683,195 A | 7/1987 | Mullis et al. | 435/6 |
| 4,683,202 A | 7/1987 | Mullis | 435/91 |
| 5,591,573 A | * 1/1997 | Whalen et al. | 435/5 |
| 5,639,730 A | 6/1997 | Eibl et al. | 514/21 |
| 6,183,999 B1 | 2/2001 | Weimer et al. | 435/91.2 |

FOREIGN PATENT DOCUMENTS

| | | |
|---|---|---|
| EP | 0131740 A2 | 1/1985 |
| EP | 0159311 A1 | 10/1985 |
| EP | 0247998 A2 | 12/1987 |
| EP | 0310229 B1 | 4/1989 |
| EP | 0320308 B1 | 6/1989 |
| EP | 0336731 B1 | 10/1989 |
| EP | 0361983 A2 | 4/1990 |
| EP | 0373960 B1 | 6/1990 |
| EP | 0447984 A1 | 9/1991 |
| EP | 0506651 A2 | 9/1992 |
| EP | 0519901 A2 | 12/1992 |
| EP | 0590327 A2 | 4/1994 |
| EP | 0637451 A1 | 2/1995 |
| EP | 0714988 A2 | 6/1996 |
| EP | 0922771 A2 | 6/1999 |
| WO | WO88/09814 | 12/1988 |
| WO | WO91/09944 | 7/1991 |
| WO | WO94/13329 | 6/1994 |
| WO | WO96/35437 | 11/1996 |

OTHER PUBLICATIONS

Lefrere et al. Journal of Virological Methods. 1999; 80: 33–44.*
Zimmerman et al. Apr. 2000. Biotechniques; 28 (4): 694–696, 698–702.*
Besnard et al., J. Clin. Microbiol. 32(8): 1887–1893 (1994).
Holodniy et al., J. Clin. Microbiol. 29(4): 676–679 (1991).
Mcomish et al., J. Clin. Microbiol. 31(2): 323–328 (1993).
Mulder et al., J. Clin. Microbiol. 32(2): 292–300 (1994).
Pyra et al., Proc. Natl. Acad. Sci. USA 91: 1544–1548 (1994).
Saldanha et al., J. Med. Virol. 43: 72–76 (1994).
Wu et al., Genomics, 4: 560–569 (1989).
Zeldis et al., J. Clin, Invest. 84: 1503–1508 (1989).
Biologicals, 20: 159–164 (1992).
Romeo et al., Hepatology 17(2): 188–195 (1993).
European Pharmacopoeia, Second Edition, (1994), pp. 853–1–853–4.
Matsuura et al., The Lancet, vol. 340, Aug. (1992), pp. 305–306.
Morbidity and Mortality Weekly Report, vol. 43, No. 28, Jul. (1994), pp. 505–509.
Gerritzen et al., Thromb. Haemost., vol. 68(6), (1992), p. 781.
Piatak et al., Science, vol. 259, Mar. (1993), pp. 1749–1754.
Eder et al., The Role of the Chimpanzee in Research, (1994), pp. 156–165.
Mullis et al., Methods in Enzymology, vol. 155 (1987), pp. 335–351.
Powell et al., Cell, vol. 50, Sep. (1987), pp. 831–840.
Kawasaki et al., Proc. Natl. Acad. Sci. USA, vol. 85, Aug. (1988), pp. 5698–5702.
Guatelli et al., Proc. Natl. Acad. Sci. USA, vol. 87, Mar. (1990), pp. 1874–1878.
Kwoh et al., Proc. Natl. Acad. Sci. USA vol. 86, Feb. (1989), pp. 1173–1177.
Lizardi et al., Tibtech, vol. 9, Feb. (1991), pp. 53–58.
Urdea et al., Nucleic Acids Research, Syposium Series. No. 24, (1991), pps. 196–201.
Pachl et al., Quantitative Detection of HIV RNA in Plasma Using a Signal Amplification Probe Assay, Program and Abstracts of the 32nd Interscience Conference on Antimicrobial Agents and Chemotherapy (1992).
Heide et al., The Plasma Proteins, Second Edition, vol. 3, (1977), pp. 545–597.
Prince et al., Eur. J. Epidemiol., vol. 3, No. 2, Jun. (1987) pp. 103–118.
De Franchis et al., Nucleic Acids Research, vol. 16, No. 21, (1988), p. 10355.
Beutler et al., Biotechniques, vol. 9, No. 2, (1990), p. 166.
Ratner et al., Nature, vol. 313, Jan. (1985), pp. 277–284.
Kaneko et al., Journal of Clinical Microbiology, vol. 27, No. 9, Sep. (1989), pp. 1930–1933.
Carman et al., The Lancet, Sep. (1989), pp. 588–591.

(List continued on next page.)

Primary Examiner—James Housel
Assistant Examiner—Shanon Foley
(74) Attorney, Agent, or Firm—Heller Ehrman White & McAuliffe

(57) ABSTRACT

A method for producing a pool of biological samples that is quality assured with respect to the load with microorganisms, using a nucleic acid amplification method, in which a screening pool is tested with a high sensitivity nucleic acid amplification method and can be divided into screening subpools, which are tested with a less sensitive nucleic acid amplification method, where individual samples can be picked out and eliminated, is described.

10 Claims, No Drawings

OTHER PUBLICATIONS

Han et al., Proc. Natl. Acad. Sci. USA, Mar. (1991), vol. 88, pp. 1711–1715.

Fujiyama et al., Nucleic Acid Research, vol. 1, No. 13, (1983), pp. 4601–4610.

Shimizu et al., Proc. Natl. Acad. Sci. USA, vol. 90, Jul. (1993), pp. 6037–6041.

Livak et al., PCR Methods and Applications, pp. 357–362, Cold Spring Harbor Laboratory Press (1995).

Sibrowski et al., Beitr Infusionsther. Basel. Karger 26: 22–26 (1990).

Mortimer, Vox Sang 73: 93–96 (1997).

* cited by examiner

SEQUENCE LISTING

<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
gacagttatc tgaccacccc ca        22

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gctaacttgc ccaggcttgt        20

<210> SEQ ID NO 3
<211> LENGTH: 31
<212> TYPE: DNA
<213> ORGANISM: Artificial Sequence
<220> FEATURE:
<223> OTHER INFORMATION: PCR primer

<400> SEQUENCE: 3
ccagtagcag tcatgcagaa cctagaggag a        31

METHOD FOR PRODUCING A QUALITY ASSURED BIOLOGICAL SAMPLE AND COMPOSITION CONTAINING THE SAME

The invention relates to a method for producing a pool of biological sample with assured quality with respect to the load of microorganisms, using nucleic acid amplification methods.

Biological samples, such as plasma donations or batches of cell culture supernatants, can be contaminated with undesired microorganisms, especially viruses or foreign DNA. These contaminations can lead to undesired reactions in preparations that are produced from such biological preparations and are administered to humans.

Above all, human plasma is of extraordinary clinical importance as a starting material for producing plasma derivatives, especially for substitution therapy in a hereditary or;acquired deficiency of plasma components. Pharmaceutical preparations of this kind as a rule are not produced from single donations, but rather from a plasma pool consisting of a very large number of individual donations.

However, when using human plasma care must be taken that it does not contain any infectious agents that could be transferred with the pharmaceutical preparation or with the plasma derivatives. Among infectious agents that could possibly be in the blood are above all viruses that can be transferred through the blood (hematogenic viruses), for example, HI-viruses or hepatitis viruses (A, B, C, D, E or G) as well as parvovirus.

Because of the great demand for drugs that contain plasma derivatives economical production of these drugs is possible only on an industrial scale.

Plasma is obtained from donors and pooled for the production of pharmaceutical preparations. A usual pool consists of about 2000–6000 individual plasma donations. Here there is the risk that the total plasma pool will become contaminated by a single virus-contaminated plasma donation. Although there was already success in processing human albumin to a virus-safe preparation by heating by the end of the first half of the $20^{th}$ century, this was initially not possible with all other drugs obtainable from plasma because of their sensitivity to heat. To this day, although there have been millions of uses of adequately prepared albumin preparations, there have never been infections with viruses occurring in the blood in humans.

In contrast, several viral infections, especially with hepatitis viruses, have been reported with many other drugs produced from plasma and since the 1980s there have been increasing reports of infections with the AIDS virus.

Around 1980 heat treatments were carried out for the first time with the appropriately stabilized factor VIII concentrates with the intention of achieving inactivation of viral contaminants by this. However, at first one had to accept a large loss of factor VIII activity and the actual inactivation potential remained unknown, respectively.

Finally, through improvement of the heat inactivation methods and the use of other new inactivation methods it was possible to produce drugs from plasma that in most cases did not lead to viral infections in the receiver. This development also went hand in hand with improvement of the donor and donation selection with the goal of excluding every donor and donation in which the possibility of viremia and thus a virus-containing plasma existed.

Since a long time it has been attempted either through detection of antigens or antibodies to or against a certain virus in the blood to exclude those donations which give a positive result and not to introduce them into a larger plasma pool that is intended to serve as starting material for the production of blood products. In the case of individual donors who in all tests do not have any symptoms of disease or pathological test results even though certain viruses can be present in their blood even in high concentration for a prolonged period of time. Now the occurrence of such viremias by a specific virus can be unambiguously detected with the aid of an amplification method.

A single plasma donation contaminated with viruses does of course become diluted through the pooling of plasma units, but the detection of viral genome sequences with the aid of amplification reactions is so sensitive that even in these dilutions virus genomes or their sequences respectively are unambiguously determinable, and if they, as mentioned above, fall under a certain detection limit, then they no longer have any clinical relevance as far as the possibility of an infection is concerned.

The EC guideline in accordance with the "EEC Regulatory Document Note for Guidance," Guidelines for Medicinal Products Derived from Human Blood and Plasma" (Biologicals 1992, 20: 159–164) proposes a quality assurance system for the control of plasma donors or plasma donations. Accordingly, every plasma donation has to be tested with validated tests for the absence of viral markers! such as hepatitis B antigen, HIV-1 and HIV-2 antibodies, since these are an indication of a corresponding viral infection of the plasma donor. Tests to exclude hepatitis C infection are also to be conducted.

According to the European Pharmacopoeia, special tests are supposed to be carried out to determine hepatitis B surface antigen, for hepatitis C virus antibody and for HIV antibodies in every donation (European Pharmacopoeia, $2^{nd}$ Edition, Part II, 1994, pp. 853–4).

The FDA guideline of Mar. 14, 1995 provides a PCR (Polymerase-Chain-Reaction) testing of an end product (immunoglobulin product) as an additional safety factor.

In spite of the proposed tests, it is stressed in the EC guideline that the safety of individual plasma donations by a control of all these virus markers alone is not sufficient. Even if the absence of the said markers in a plasma sample is confirmed, viremia of the donor cannot be excluded. Viral antigens and the corresponding antibodies are not always immediately detectable after an infection. The first markers for a viral infection mostly do not arise until weeks or months after a contact with an infectious material. This critical period of time after an infection and before the occurrence of antibodies is generally characterized as a "window period." The time after infection in which the first viral markers are detectable, however, varies from virus to virus.

Moreover, it is also known that for many drugs produced from plasma a depletion or inactivation occurs as part of the production process and such products themselves are virus safe to a great extent.

Although virus inactivation of plasma derivatives have been carried out extremely successfully on an industrial scale. Nevertheless in rare cases there have been transmissions of hematogenic viruses like AIDS, hepatitis A, B and C. Therefore it has to be,assumed that virus-contaminated products have been produced by the manufactures in a few production batches in spite of a constant production method (Lancet 340, 305–306 (1992); MMWR 43 (28), 505–509 (1994); Thromb. Haemost. 68, 781 (1992)). The cause of this should probably be sought in an extremely high contamination of certain starting batches. Since only indirect methods are available to exclude virus-contaminated plasma donations in producing the plasma, there is the possibility that the starting material will be so highly contaminated that the otherwise successful virus inactivation and virus depletion methods are no longer sufficient to produce virus-safe end products.

Since the human infectious dosage for most human pathogenic viruses is unknown and at the present is not even determinable in testing the plasma pool, it is desired to pick out every single contamination by identifying the contaminated individual samples. The nucleic acid amplification tests that are used therefore are indeed extremely sensitive, but very costly. So their use is justified with known human pathogenic viruses, while for other microorganisms of which either no human pathogenic effect is known or described or for which only a very high pathogen dosage is infectious, this expenses would not be necessary.

In particular, WO 96/35437 and U.S. Pat. No. 5,591,573—A describe test systems for plasma pools using nucleic acid amplification methods and/or antibody testing. U.S. Pat. No. 5,591,573 discloses a method for testing plasma pools. With this method a first pool is prepared and tested by means of PCR. If this PCR test is positive, a second smaller subpool is prepared and again tested by means of PCR. This process is repeated until the contaminated individual donation is identified. Antibody testing or maintenance of preset definite limit values, disclosed as part of the screening method, are also envisioned in accordance with WO 96/35437.

However, the described nucleic acid amplification methods have in common the fact that one always attempts to use the amplification method that allows the greatest sensitivity. However, as noted, these high sensitivity PCR tests are extremely costly, in particular in serial testing of pools of individual biological samples. PCR tests with lower sensitivity, which would be far more cost favorable, however, are generally avoided in such testing, since the risk of contaminations that lie under the (low) detection limit would be concomitantly high.

Similarly, even with supernatants from recombinant cell cultures contaminations by microorganisms or by nucleic acid material from host cells continue to occur. Such contaminations should, of course, not be present or should be present only at a certain maximum value (limit value) in pharmaceutical preparations that are to be purified from the supernatants.

The task of this invention is thus to make available a method for producing a pool of biological samples using nucleic acid amplification methods that is quality assured with regard to the load of microorganisms, especially viruses, a method which on the one hand enables a reliable identification of contaminated individual samples, especially highly contaminated individual samples, as well as adherence to certain limit values for such contaminants in the pool, but on the other hand brings a cost reduction and a method that is simpler, to the pool testing methods known from the prior art.

In accordance with the invention, this task is solved by a method for producing a pool of biological samples that is quality assured with regard to the load of microorganisms using a nucleic acid amplification method which is characterized by the following steps:

Taking aliquots from the biological samples,

Combining the aliquots into a screening pool,

Testing the screening pool for the presence or the content of genome equivalents of microorganisms by means of a first nucleic acid amplification process, which has a certain selected detection limit DL-1 with respect to the microorganisms to be tested, Dividing the screening pool into screening subpools by recombining the aliquots that were taken into smaller pools when a preset limit value of genome equivalents is exceeded in testing the screening pool, Retesting the screening subpool for the presence of or the content of genome equivalents of the microorganism that is to be tested by means of an additional nucleic acid amplification process, which has a certain selected detection limit DL-2 for the microorganisms to be tested, where DL-1<DL-2, Identifying and eliminating those samples that exceed DL-2, and Combining the non-eliminated samples into a quality assured pool.

By providing for at least two nucleic acid amplification processes that differ with regard to their sensitivity in accordance with the invention an efficient (because of the high sensitivity of the pool testing) and nevertheless cost favorable method can be made available. Since testing the subpool is carried out up to the individual samples by a less sensitive nucleic acid amplification method without prior further extraction of the nucleic acid (which therefore is decisively more cost favorable and less expensive).

With the method in accordance with the invention thus in a first step the screening pool is tested for nucleic acid contamination with a very sensitive and quantitative method. The very costly determination of the contaminated individual sample or donation, which involves a very much higher number of additional tests, is determined with a less sensitive nucleic acid amplification method. In doing so, no risk is taken that a relevant contamination will be overlooked, since the screening pool testing takes place with a method that is as sensitive as possible. But, on the other hand the costs and expenditures of time of the elimination method for the contaminated individual samples or batches are decisively reduced. In those instances in which determination of such contaminated individual donations has up to now not been carried out for these reasons, the method in accordance with the invention offers for the first time the possibility to use the valuable raw material, which the individual donations represent, at low cost and keeping these samples from being discarded.

The sensitivity of the nucleic acid amplification method is set in accordance with the invention as the quantity of genome equivalents that is just still detectable with the relevant nucleic acid amplification method. Providing methods of this kind with precisely established limit values is easily possible for the man skilled in the art and is a part of his ordinary knowledge.

The method in accordance with the invention is suitable above all for quality assurance of pools with respect to the load of microorganisms, which are of low pathogenicity or toxicity or of which it can be assumed that a load that lies under the established limit value is in each case eliminated in the course of the subsequent purification process up to the preparation of the pharmaceutical preparation or that the amount of contamination corresponding to this limit value in a pharmaceutical preparation of this kind is harmless and without side effects. A particular example of this consists of contaminations with parvoviruses, in particular parvo B19.

Parvovirus B19 is a single strand DNA virus with 32 nm diameter that does not have a lipid membrane and thus is relatively resistant to virus inactivation methods. Thus, most inactivation methods, for example, physical methods like pasteurization (60° C. over 12 h) or chemical treatments like organic solvents (TNBP and/or detergents) do not have satisfactory results. Only dry heat treatment appears to have proven to be effective.

The parvovirus B19 is the causative agent of the harmless infectious erythema (erythema invectiosum), with arthralgias and arthritis occasionally being observed. Intrauterine infections are feared, since they often end with fetal death. The limited circle of B19 threatened patients include those with chronic hemolytic anemia, patients following bone marrow transplantations, patients with congenital/acquired immune deficiency as well as pregnant women (Sibrowski et al., Beitr Infusionsther. Basel, Karger, 1990, 26, 22–26).

The seroprevalence in industrial countries is 2–10% in children under 5 years of age and 40–60% in adults over 20 years of age and 85% in adults over 70 years of age. This high seroprevalence thus results in a large number of positive results in plasma pool testing, thus resulting in the need for a large number of additional tests in order to determine the highly contaminated individual samples.

EP-A-0 922 771 describes a method for detecting high virus concentrations in blood plasma, in which the sensitivity of PCR is decreased through the use of suboptimum conditions in the extraction, amplification or detection, so that the parvovirus DNA can only still just be detected in samples whose DNA content is greater than $10^6$–$10^7$ genome equivalents/mL. However, this method has the disadvantage that it is not suitable for testing pools.

Nevertheless, all of the microorganisms that occur such as bacteria or viruses can be analyzed in accordance with the invention, where above all quality assurance with respect to viruses is of particular priority in the testing of blood and plasma donations.

Preferably, hepatitis viruses, in particular HAV, HBV, HCV, HDV, HEV and HGV, retroviruses, in particular HIV-1 and HIV-2, and parvoviruses, in particular parvo B19, are tested with the method in accordance with the invention or plasma pools are quality assured with respect to these kind of viruses.

In testing various batches of a recombinant production of proteins the maintenance of certain (prescribed) limit values of the contaminations with host cell nucleic acids (here eukaryotic or prokaryotic cells or DNA or RNA are detected here as microorganisms) or contamination with certain bacterial or viral contaminations is tested.

A particularly preferred variation of the method in accordance with the invention consists of setting the limit value in testing the screening pool between the detection limit of the first nucleic acid amplification method DL-1 and $10^5$ genome equivalents/mL, where in particular a value around $10^4$ genome equivalents/mL has proved to be particularly efficient for parvo B19, for instance. Preferably the relevant limit can also be in agreement with the relevant detection limit.

The detection limit for the first nucleic acid amplification method DL-1 preferably lies in the range of $10^2$–$10^4$ genome equivalents/mL (however, it can be up to 10–50 GE/mL or, in exceptional cases, even lower), whereas the detection limit DL-2 is usually chosen to be $10^4$–$10^7$ genome equivalents/mL. DL-1 and DL-2 preferably differ by at least one power of ten, but a difference of about two powers of ten has proved to be particularly efficient in accordance with the invention, since in this way the contaminated individual donations can still be reliable identified (this is necessary in accordance with the invention) and on the other hand the costs and expenses for the screening process can be reduced considerably compared to the known methods.

The amplification of nucleic acids can in accordance with the invention take place by a series of amplification processes that are described in the literature; the PCR method has proved to be particularly effective here and because of its widespread usage and industrial availability as well as its costs it is also preferred. The PCR amplification method was first described in 1983 by Mullis et al. (U.S. Pat. No. 4,683,195 and U.S. Pat. No. 4,683,202). Viral genome sequences can also be amplified by "nested PCR" (Methods Enzymol. 155 (1987), 335–350). For amplification and detection of RNA the RNA must first be transcribed to DNA. This method is conducted using reverse transcriptase and is called RT-PCR (Cell 50 (1987), 831–840).

The analysis of the amplification products can take place through the use of labeled nucleotides or oligonucleotide primers in an elongation process and subsequent hybridization or gel electrophoretic separation of the products.

Detection of amplified DNA fragments can take place, for example, by means of a probe that carries two fluorescence dyes. This method is described, for example, by Livak et al. (PCR Method and Appl. 1995; 4:357–362). The particular property of this probe lies in the fact that the fluorescence of the dye (FAM) attached at the 5' end of the probe, the reporter, is reduced by the presence of the second fluorescence dye (TAMRA), the quencher, which is arranged at the 3' end of the primer.

In the course of the amplification the new DNA strand is now synthesized under the effect of a thermostable DNA polymerase, preferably Taq polymerase. In doing so the DNA polymerase displaces the probe not only from the individual strand, but;rather decomposes it by means of its endonucleolytic activity and thus releases the two fluorescence dyes. The fluorescence of the reporter dye is no longer suppressed by the quencher dye and increases. This increase of fluorescence is continuously recorded in the ABI prism 7700 in the course of the PCR. The threshold value, starting with which an increase of fluorescence is evaluated as a positive signal, is measured in comparison with several negative controls.

Quantification of the load with the microorganism, for example parvo B19, in an unknown sample takes place via an external calibration curve. A cloned piece of the parvo B19 DNA in a carrier plasmid, which includes the sequence to be amplified; is additionally coamplified in linearized form in concentrations of $10^6$ copies/reaction up to 10 copies/reaction. By establishing a threshold value (corresponding to one PCR cycle in which the fluorescence signal of the reporter dye first rises above the baseline) a calibration line is established in the program with which the content of parvo B19 DNA of an unknown sample above its threshold value is quantified.

Alternate methods for PCR include the ligase chain reaction (LCR), in correspondence with EP 0 320 308 A and EP 0 336 731 A, and nucleic acid sequence based amplification (NASBA), self-sustained sequence replication (SSR), in correspondence with EP 0 310 229, or the transcription based amplification system (TAS) in correspondence with EP 0 373 960 A. A number of enzymes that can be used simultaneously or stepwise in the amplification such as a DNA polymerase or an RNA polymerase are used in these methods.

Preferably in accordance with the invention, internal standards, with which the basic functioning of the amplification can be guaranteed, can be added in the nucleic acid amplification. In routine tests the interpretation of the results obtained with the method in accordance with the invention can usually be traced as follows:

a) no detection of the internal standard (i.e., no visible bands): the determination did not function, for example, as a result of the amplification reaction (for example, the PCR); in this way false negative results can be excluded.

b) only the internal standard is detectable (for example, only the standard band is visible): the determination, including the amplification reaction (for example, the PCR), functioned, the sample is negative;

c) standard and sample nucleic acid are detectable (for example, both bands are visible): positive sample.

The biological samples that are priority for testing in accordance with the invention are selected from the group of individual blood donations, plasma, serum or cell culture batches. The expected contaminations occur particularly with these biological samples and these are also used with priority in the industrial manufacture of drugs from biogenic sources.

The method in accordance with the invention can be carried out in an automated version using robotic control, with conventional platforms being particularly suitable for this. The man skilled in the art is aware of many different possibilities for producing such screening pools. For example, Mortimer (Vox. Sang. 1997, 73:93–96) describes two dimensional (2D), three dimensional (3D) and even four dimensional (4D) pools. In order to resolve, for example, a 3D pool produced from 512 (8×8×8) individual samples now, one has to use, for example, 24 subpools in order to be able to identify unambiguously a contaminated individual sample.

In accordance with the invention, the second nucleic acid amplification process is preferably carried out directly from the subpool after the first nucleic acid amplification. This means that no additional extraction of the nucleic acid takes place, but rather it is determined directly in the subpool.

In accordance with another aspect, this invention also concerns a quality assured pool of biological samples, which can be obtained through the method in accordance with the invention, as well as a pharmaceutical preparation that is produced or can be produced on the basis of a quality assured preparation in accordance with the invention. These pharmaceutical preparations preferably contain at least one component selected from the group of proteins, in particular plasma proteins as well as recombinantly produced proteins, and enzymes.

The invention is illustrated in more detail below by means of the following example, to which it, however, is not intended to be limited.

EXAMPLE

Pooling

Aliquots of 512 plasma donations are pooled by means of a three dimensional scheme to a screening pool and 24 subpools.

Extraction

The nucleic acid extraction from a screening pool is carried out by means of a modified protocol of the QIAmp viral kit from QIAGEN. For this 1 mL of the screening pool is subjected to ultracentrifugation, the supernatant is reduced to 140 µL. After the addition of 560 µL AVL lysis buffer in accordance with the QIAGEN kit the mixture is incubated for 10 min at 56° C. in a thermal shaker. The lysate is applied to a silica column and forced through the column by centrifuging it at 8000 rpm. After washing with 0.5 mL wash buffer AW1 and AW2 each, the nucleic acid adsorbed to the column is eluted with 50 µL $H_2O$.

Amplification

A small fragment of parvo B19 DNA is amplified by addition of 20 µL extract to 30 µL Mastermix.

(Perkin Elmer, TaqMan PCR Core Reagent Kit with 5 µL 10×TaqMan Buffer, 14 µL 25 mM $MgCl_2$, 4 µL 2.5 mM dNTPs, 1.5 µL 10 µM PT1.f(5'GACAGTTATCTGACCACCCCCA3') (Seq. ID Nr. 1), 1.5 µL 10 µM PT1.r(5'GCTAACTTGCCCAGGCTTGT3') (Seq. ID Nr. 2), 1 µL 5 µM PT1.p(5'6-FAM-CCAGTAGCAGTCATGCAGAACCTAGAGGAGATAMRA3') (Seq. ID Nr. 3), 1 µL Tween 20 (1%), 1.25 µL gelatin (2%), 0.5 µL AmpErase UNG (1 U/µL), 0.25 µL AmpliTaq Gold (5 U/µL).

The amplification takes place under the following conditions in an ABI prism 7700:

1. AmpErase UNG reaction 2 min, 50° C.
2. Initial denaturing 10 min, 95° C.
3. Cycles of 15 sec at 95° C. and 1 min at 58° C.

The PCR is evaluated by the increase of fluorescence during the PCR. The threshold value (i.e., the cycle at which the signal increases above the ground noise) serves for quantification. The threshold values of a standard series of a linearized plasmid with a cloned fragment of parvo B19 genome in this case serves as the baseline for measuring the parvo B19 concentration in the extract of the screening pool.

If the number of genome equivalents measured in the sample lies below the limit value of $10^4$ GE/mL in the screening pool, the samples contained in this pool are cleared for use. On the other hand, if a value over the limit value is reached, the screening pool is resolved.

Resolution

The 24 subpools of a screening pool are diluted 1:200 in $H_2O$ (distilled) in several steps by means of a robot and used without extraction in the TaqMan PCR.

Amplification of the Resolution

A small fragment of parvo B19 DNA is amplified by addition of 20 µL subpool dilution (corresponds to 0.1 µL of the subpool) to 30 µL Mastermix.

(Perkin Elmer, TaqMan Gold Kit with 5 µL 10×TaqMan buffer, 14 µL 25 mM $MgCl_2$, 4 µL 2.5 mM dNTPs, 1.5 µL 10 µM PT1.f(5'GACAGTTATCTGACCACCCCCA3'), 1.5 µL 10 µM PT1.r(5'GCTAACTTGCCCAGGCTTGT3'), 1 µL 5 µM PT1.p(5'6-FAMCCAGTAGCAGTCATGCAGAACCTAGAGGAGA-TAMRA3'), 1 µL Tween 20 (1%), 1.25 µL gelatin (2%), 0.5 µL AmpErase UNG (1U/µL), 0.25 µL AmpliTaq Gold (5 U/µL).

The amplification takes place under the following conditions in an ABI prism 7700:

1. AmpErase UNG reaction 2 min, 50° C.
2. Initial denaturing 10 min, 95° C.
3. Cycles of 15 sec at 95° C. and 1 min at 58° C.

Evaluation

The PCR is evaluated by the increase of fluorescence during PCR. By determining the threshold value (i.e., the cycle at which the signal rises above the ground noise) in comparison with the values of a known standard series that was amplified at the same time, the number of genome equivalents in the extract of the screening sample is determined.

Since only samples with a content of at least $10^4$ GE/mL can produce a signal if the supply is 0.1 µL material, all individual donations recognized as positive in the resolution are discarded and the residual are released for use.

What is claimed is:

1. A method for producing a pool of quality assured biological samples comprising:
   (a) testing a screening pool for the presence of a parvovirus genome equivalent, wherein the testing is performed by a first nucleic acid amplification process that has a detection limit (DL-1) for parvovirus, wherein the screening pool comprises collected aliquots from a plurality of biological samples, and wherein the testing determines whether the screening pool has a content of genome equivalents that exceeds a preset limit;
   (b) forming screening subpools from the screening pool of (a) that have a content of genome equivalents that exceed the preset limit; wherein the screening subpool is comprised of aliquots from a portion of the plurality;
   (c) testing the subpools of (b) for the presence of a parvovirus genome equivalent, wherein the testing is performed by a second nucleic acid amplification process that has a detection limit (DL-2) for parvovirus, wherein DL-1 is lower than DL-2;
   (d) eliminating samples corresponding to subpools that have a genome equivalent content that exceeds DL-2; and
   (e) combining the remaining samples to produce the pool of quality assured biological samples.

2. The method according to claim 1, wherein the first nucleic acid amplification process comprises a polymerase chain reaction.

3. The method according to claim 1, wherein the preset limit is no more than $10^5$ genome equivalents per milliliter.

4. The method according to claim 3, wherein the preset limit is about $10^4$ genome equivalents per milliliter.

5. The method according to claim 1, wherein the biological samples are obtained from a source selected from the group consisting of blood, plasma, serum and cell culture batches.

6. The method according to claim 1, wherein the screening pool is formed from aliquots from 512 biological samples, and the subpools are formed from aliquots from 24 biological samples.

7. The method according to claim 1, wherein the second nucleic acid amplification process is performed immediately after performance of the first nucleic acid amplification process.

8. The method according to claim 1, wherein the parvovirus is parvovirus B-19.

9. (Previously amended) The method according to claim 1, wherein DL-1 is $10^2$ to $10^4$ genome equivalents per milliliter and DL-2 is $10^4$ to $10^7$ genome equivalents per milliliter, respectively.

10. The method according to claim 9, wherein DL-2 is at least ten times greater than DL-1.

\* \* \* \* \*